(12) United States Patent
Jabbarzadeh et al.

(10) Patent No.: US 11,866,685 B2
(45) Date of Patent: Jan. 9, 2024

(54) TEMPERATURE RESPONSIVE DEVICE FOR MECHANOBIOLOGICAL MANIPULATION

(71) Applicant: UNIVERSITY OF SOUTH CAROLINA, Columbia, SC (US)

(72) Inventors: Ehsan Jabbarzadeh, Columbia, SC (US); Christopher Wu, Matthews, NC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 646 days.

(21) Appl. No.: 16/939,685

(22) Filed: Jul. 27, 2020

(65) Prior Publication Data
US 2021/0095238 A1    Apr. 1, 2021

Related U.S. Application Data

(60) Provisional application No. 62/942,917, filed on Dec. 3, 2019, provisional application No. 62/906,759, filed on Sep. 27, 2019.

(51) Int. Cl.
*C12M 1/34*      (2006.01)
*C12M 1/12*      (2006.01)
(Continued)

(52) U.S. Cl.
CPC ............ *C12M 41/12* (2013.01); *C12M 23/20* (2013.01); *C12M 25/14* (2013.01); *C12M 35/02* (2013.01);
(Continued)

(58) Field of Classification Search
None
See application file for complete search history.

(56) References Cited

U.S. PATENT DOCUMENTS

| 4,851,354 A | 7/1989 | Winston et al. |
| 6,942,873 B2 | 9/2005 | Russell et al. |

(Continued)

FOREIGN PATENT DOCUMENTS

| WO | WO-2011035177 A2 * | 3/2011 | ......... G01N 33/5008 |
| WO | WO-2014142161 A1 * | 9/2014 | ............. C12M 23/12 |

OTHER PUBLICATIONS

Tekin et al., "Stimuli-responsive microwells for formation and retrieval of cell aggregates", Lab Chip, 2010, 10, 2411-2418. (Year: 2010).*

(Continued)

*Primary Examiner* — William H. Beisner
(74) *Attorney, Agent, or Firm* — DORITY & MANNING, P.A.

(57) ABSTRACT

Biocompatible, mechanically-dynamic thermoresponsive devices, methods for forming the devices, and exemplary applications for the devices are described. The devices include a series of wells therein and provide for temperature-controlled mechanostimulation of single cells or groups of cells that can be retained in the wells of a device. Mechanostimulation can be single instance of any duration, continuous, or regular or irregular cyclic mechanostimulation of single cells, cell clusters, cell spheroids, or organoids and may be utilized in any of a variety of biomedical applications including, without limitation, cellular engineering, cellular phenotyping, and drug discovery/screening.

24 Claims, 13 Drawing Sheets

(51) Int. Cl.
   *C12M 1/42* (2006.01)
   *C12M 1/00* (2006.01)
   *C12M 1/32* (2006.01)
   *C08L 33/26* (2006.01)
   *C08L 33/10* (2006.01)

(52) U.S. Cl.
   CPC ............. *C12M 35/04* (2013.01); *C08L 33/10* (2013.01); *C08L 33/26* (2013.01); *C12M 23/12* (2013.01)

(56) References Cited

U.S. PATENT DOCUMENTS

| | | | |
|---|---|---|---|
| 7,494,482 | B2 | 2/2009 | Orgill et al. |
| 8,323,920 | B2 | 12/2012 | Liulevych et al. |
| 9,494,575 | B2 | 11/2016 | Jin et al. |
| 2007/0026518 | A1* | 2/2007 | Healy .................. C12N 5/0068 435/325 |
| 2013/0089869 | A1 | 4/2013 | Blobe et al. |
| 2014/0356336 | A1* | 12/2014 | Egusa .................. C07D 309/30 435/325 |
| 2019/0055590 | A1 | 2/2019 | Yonemitsu et al. |
| 2019/0144830 | A1* | 5/2019 | Cha .................... C12N 5/0663 435/394 |

OTHER PUBLICATIONS

Tekin et al., "Controlling Spatial Organization of Multiple Cell Types in Defined 3D Geometries", Adv. Mater. 2012, 24, 5543-5547. (Year: 2012).*
Tekin et al., "Responsive Micromolds for Sequential Patterning of Hydrogel Microstructures", J. Am. Chem. Soc. 2011, 133, 12944-12947. (Year: 2011).*
Baneyx, F. "Recombinant protein expression in *Escherichia coli*" *Curr. Opin. Biotech.* 10 (1999) pp. 411-421.
Boussommier, A. "3D Cell Culture: Market and Industrial Needs" *ElveFlow* (2019) pp. 1-15.
Choi, et al. "A temperature-sensitive drug release system based on phase-change materials" *Angew Chemie Int'l Ed.* 49 (2010) pp. 7904-7908.
Derfus, et al. "Intracellular delivery of quantum dots for live cell labeling and organelle tracking" *Adv. Mater.* 16 (2004) pp. 961-966.
Dhar, et al. "Polyvalent Oligonucleotide Gold Nanoparticle Conjugates as Delivery Vehicles for Platinum (IV) Warheads" *J. Am. Chem. Soc.* 131 (2009) pp. 14652-14652.
Gardel, et al. "Mechanical response of cytoskeletal networks" *Meth. Cell Biol.* 89 (2008) pp. 487-519.
Lewis, et al. "The effect of cyclic mechanical strain on activation of dendritic cells cultured on adhesive substrates" *Biomaterials* 34 (2013) pp. 9063-9070.
Li, S. "Electroporation gene therapy: new developments in vivo and in vitro" *Curr. Gene Ther.* 4 (2004) pp. 309-316.
Llucia-Valldeperas, et al. "Unravelling the effects of mechanical physiological conditioning on cardiac adipose tissue-derived progenitor cells in vitro and in silico" *Sci. Rep.* 8:499 (2018).
Mathur, et al. "In vitro cardiac tissue models: Current status and future prospects" *Adv. Drug Deliv. Rev.* 96 (2016) pp. 203-213.
Medgadget. "Medgadget's Best Medical Technologies of 2018" (2018) pp. 1-17.
Miller, et al. "Mechanical DNA delivery by ultrasonic cavitation" *Somat. Cell Mol. Genet.* 27 (2002) pp. 115-134.
Mitchell, et al. "Poly(N-isopropylacrylamide) Hydrogels for Storage and Delivery of Reagents to Paper-Based Analytical Devices" *Chromatography* 2 (2015) pp. 436-451.
Rossy, et al. "Role of Mechanotransduction and Tension in T Cell Function" *Front. Immunol.* 9:2638 (2018) pp. 1-11.
Sharei, et al. "A vector-free microfluidic platform for intracellular delivery" *PNAS* 110 (2013) pp. 2082-2087.
Slowing, et al. "Mesoporous silica nanoparticles for intracellular delivery of membrane-impermeable proteins" *J. Am. Chem. Soc.* 129 (2007) pp. 8845-8849.

* cited by examiner

TEMPERATURE RESPONSIVE DEVICE FOR MECHANOBIOLOGICAL MANIPULATION

CROSS REFERENCE TO RELATED APPLICATION

This application claims filing benefit of U.S. Provisional Patent Application Ser. No. 62/906,759, entitled "Temperature Responsive Cell Culture Platform for Mechanobiological Manipulation," having a filing date of Sep. 27, 2019, and of U.S. Provisional Patent Application Ser. No. 62/942,917, entitled "Temperature Responsive Device for Mechanobiological Manipulation," having a filing date of Dec. 3, 2019, both of which are incorporated herein by reference in their entirety.

FEDERAL RESEARCH STATEMENT

This invention was made with government support under Grant No. R03 EB026813, awarded by the National Institutes of Health. The government has certain rights in this invention.

BACKGROUND

Physical manipulation of cell membranes has been utilized for several different applications. For instance, a microfluidics system has been developed for causing perturbations in a cell membrane (SQZ Biotech® Cell Therapy Platform) as an alternative to common methods for delivery of agents to cell interiors (i.e., viral transfection, electroporation, sonoporation, cell-penetrating peptides). The SQZ system includes a microfluidic channel that is configured such that a cell suspended in a buffer can pass therethrough. The microfluidic channel includes a cell-deforming constriction with the size of the constriction being a function of the diameter of the cell. The system has demonstrated the potential for vector-free delivery of materials to difficult-to-transfect cell types, including stem cells and immune cells. Unfortunately, the microfluidic platform places shear forces on cell membrane that can decrease cell viability. Furthermore, the deformation duration is limited to the time individual cells spend in the constriction, which is dependent on both cell flow rate and constriction length. Both cell flow rate and constriction length will be constrained by physical properties of the system and both can also affect other variables, including shear forces, leading to unintended and undesirable effects. Moreover, the device is unable to assess effects of heterogenous cell deformation, for instance on membrane disruption, as the constriction is homogenous across all experimental samples.

An approach for studying cells by use of cell membrane perturbation includes retaining cells in an optically transparent well that is mechanically coupled with a ported, airtight reservoir that can be filled with pressurizing media to create cyclic variations in hydrostatic pressure. This cycling pressure is used to deform the well and thereby exert a substantially uniform biaxial strain on the cells attached to the deformed surface (see, e.g., U.S. Pat. No. 4,851,354).

Other methods and devices have been developed for transmitting micromechanical forces locally in order to induce surface convolutions into tissues on the millimeter to micron scale for promoting wound healing (see, e.g., U.S. Pat. No. 7,494,482).

While the above describes improvement in the art, room for further improvement exists. For instance, methods and devices that can provide well-controlled mechanically-induced cellular deformation could be beneficial in applications such as for delivery of agents to cell interiors, to induce secretions from cells, to study cellular responses to deformation such as membrane diffusion kinetics and actin restructuring, and to induce phenotype changes in cells, just to name a few. Methods and devices that could provide for well-controlled low shear sustained or cyclic cellular mechanical deformation would be of great benefit in the art.

SUMMARY

According to one embodiment, disclosed is a thermoresponsive device that includes a supporting base layer and a well layer at a surface of the supporting base layer. The well layer defines a well therein that includes one or more walls formed of a polymeric composition that including a thermoresponsive polymer. For instance, a wall of the well can be formed of an interpenetrating polymer network (IPN), and the IPN can include a thermoresponsive polymer and a second polymer.

Also disclosed is a method for forming a thermoresponsive device. For instance, a method can include applying a precursor solution to a supporting base layer to form a well layer. A method can also include polymerizing one or more components of at least a portion of the precursor solution to form a polymeric composition that includes a thermoresponsive polymer. A method can further include removal of a portion of the well layer; for instance, removing unpolymerized precursor solution, i.e., a portion of the precursor solution that was not subjected to polymerization, and thereby forming a well in the well layer, the well including one or more walls formed of the polymeric composition that includes the thermoresponsive polymer.

A method for examining a cell is also described. For instance, a method can include locating a cell within a well of a thermoresponsive device as described. The examination method can also include modifying a temperature of the device, upon which the volume of the well can be modified, thereby causing a mechanostimulation of the cell held in the well. Beneficially, disclosed methods can be utilized to examine single cells of any type, as well as groups of cells comprised of a single cell type or multiple cell types, e.g., cell clusters, cell spheroids, cell organoids, etc., under any desired mechanostimulation protocol, e.g., single dose, sustained, cyclical, etc.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
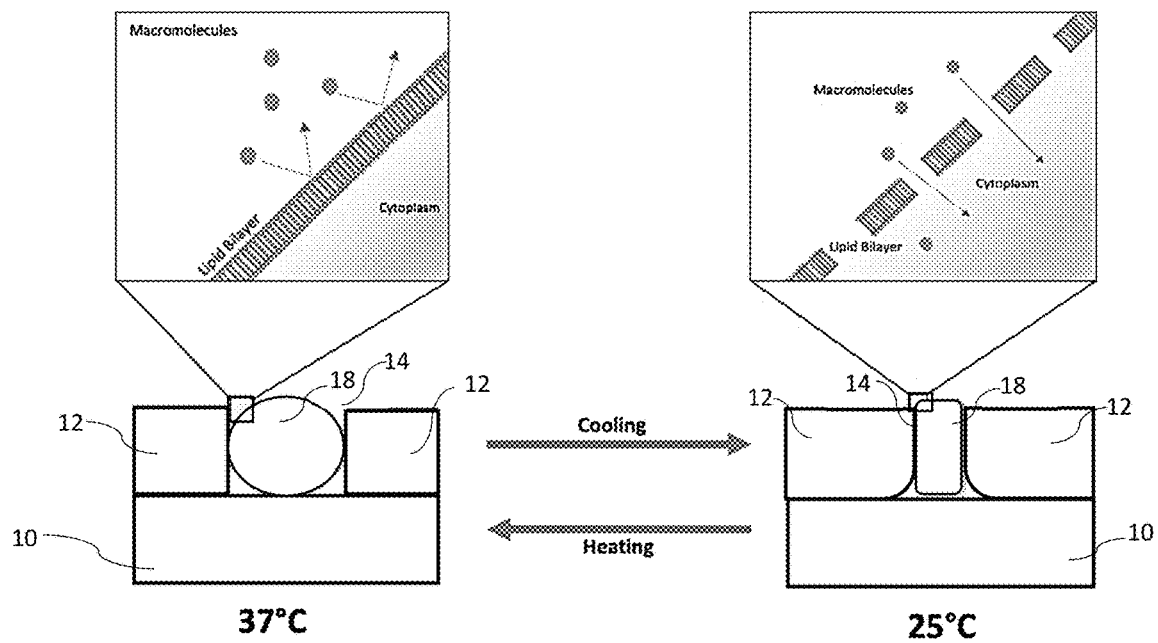
FIG. 1 schematically illustrates a well of a thermoresponsive device as described herein in which cell deformation due to well size modification with change in temperature deforms the cell wall and in one embodiment generates formation of transient membrane pores in the cell wall of a cell held in the device.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

Provided are biocompatible, mechanically-dynamic thermoresponsive devices, methods for forming the devices, and exemplary applications for the devices. The devices can define a plurality of wells therein and can provide for controlled mechanostimulation of single cells or groups of cells that can be retained in the wells of a device and/or for controlled release of materials retained within the device. For instance, a device can provide for a single instance of mechanostimulation of any duration, or for continuous, or regular or irregular cyclic mechanostimulation of single cells, cell clusters, cell spheroids, or organoids and may be utilized in any of a variety of biomedical applications including, without limitation, cellular engineering, cellular phenotyping, and drug discovery/screening.

During use and upon a change in local temperature, the volume of the wells can vary in a predetermined fashion based upon the nature of the polymeric composition used to form the wells. The temperature-controlled volume provides a route for mechanobiological manipulation of cells retained in the wells, as well as provides a route for release of agents retained within the wells, from cells retained within the wells, and/or from the polymeric composition forming the well layer. During use, mechanostimulation of cells held in the wells (alternatively referred to herein as microwells) can be controlled by control of local temperature of the device. Beneficially, the microwell volume change can be reversible and well-controlled, and as such, any desired protocol can be designed incorporating single burst, sustained, intermittent, or cyclical well volume modification, as well as any combination thereof. Moreover, the amount of well volume modification with temperature change can also be controlled and can be used to impart higher or lower deformation forces on a cell retained therein, as desired. The variety of designs possible in disclosed devices can provide for customized regimes and for control over applied forces in such regimes that have not been possible with previously known systems. As such, the devices can be utilized for well-controlled cellular mechanostimulation, as well as for well-controlled release of agents from the devices.

The thermoresponsive devices can have a number of advantages as compared to previously known systems and devices. For instance, the microwells of the devices can be formed to have any of a large variety of shapes, including heterogeneous cross-sectional shapes (e.g., triangles, squares, stars), as well as homogeneous cross-sectional shapes (e.g., circular). Heterogeneously-shaped microwells can be utilized to induce heterogeneous deformation in a cell held within a well, which can provide a variety of interesting and beneficial effects. For instance, heterogeneous mechanostimulation of a cell can induce increased membrane poration/disruption at select membrane regions that are subjected to increased deformation as compared to other regions of the cell membrane. Moreover, through induction of heterogenous deformation forces across the cell membrane, regions of the cell membrane that may be subject to membrane disruption due to high deformation force can be limited to those regions of high force, which can decrease the number of potential sites requiring membrane repair and thus, lower occurrences of cell injury and death.

Disclosed devices can also be formed with high homogeneity between individual wells and as a result can provide improved protocol homogeneity. More specifically, the homogeneity possible between individual microwells of a device can ensure that all materials (cells, materials, etc.) that are retained in the wells can receive essentially the same mechanostimulation in terms of both force and duration, a fundamental property that is not met by current mechanostimulation products.

The temperature-responsive devices can also provide high cell viability. For instance, a protocol utilizing disclosed devices can exhibit a percent cell viability of about 75% or greater, about 80% or greater, about 90% or greater, or about 95% or greater, in some embodiments. In addition, in those protocols in which a device is utilized to deliver an agent into or out of cells retained by the device, the devices can provide for statistically-significant high quantities of agent delivery.

The control capabilities provided by the devices can be utilized to control morphology of cells treated in the devices. For instance, the retention of stem cell morphology after a deformation treatment can be highly desirable, as differentiation can be viewed as unfavorable in some embodiments; for instance, when assessing intracellular delivery. Due to the excellent control afforded by disclosed devices, not only in terms of device design (e.g., cell size, shape, homogeneity) but also in terms of protocol control (e.g., timing, location, and magnitude of applied forces), cell characteristics can be better controlled and understood. For instance, it is generally desirable that adherent cells can adhere to a testing device with little to no effect on the cells' metabolic activity. Due to the variations possible in formation (materials, well shapes, well size, etc.), disclosed devices can be designed to encourage attachment of adherent cells within wells for extended experiments related to cell deformation while lessening the risk of cell death.

Figure 2:
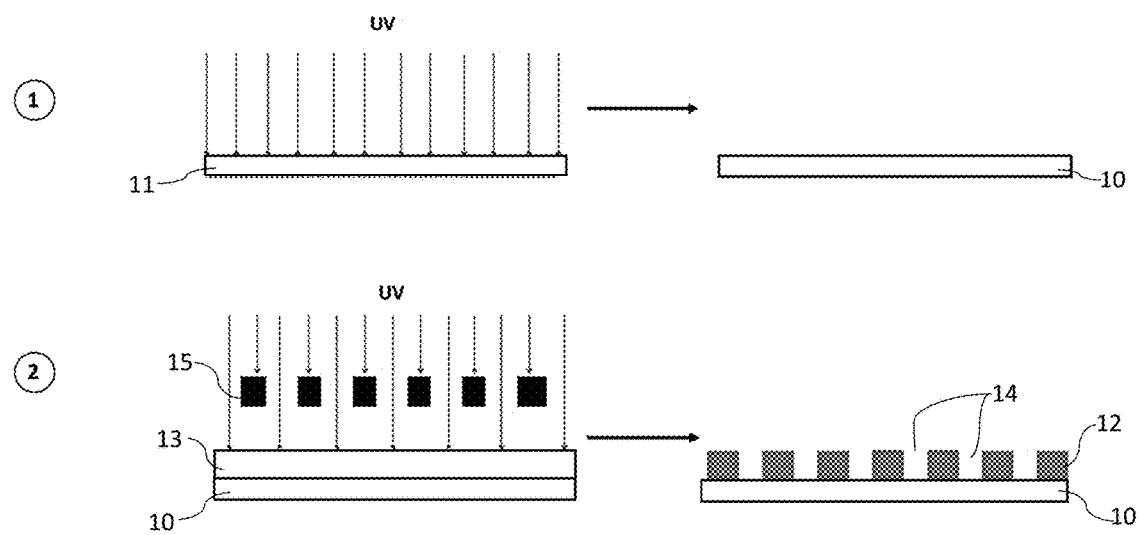
FIG. 2 schematically illustrates one method for forming a thermoresponsive device as described herein by use of a photopolymerization approach.

As illustrated in FIG. 1, a thermoresponsive device can include a supporting base layer 10 and a well layer 12 at a surface of the base layer 10. The well layer can define a well 14 within the layer that can be sized to retain one or more cells 18. While a single well 14 is illustrated in FIG. 1, it should be understood that a device can generally include a plurality of wells 14 in an array, for instance as illustrated in FIG. 2.

The largest size of the wells 14 at room temperature (e.g., about 25° C.) (i.e., without any temperature-controlled volume loss or with any temperature-controlled volume increase) can generally depend upon the nature of the use of the device. For instance, when considering retention of an agent for delivery or an individual cell 18 in a well 14 as illustrated in FIG. 1, the well 14 can have a room temperature largest cross-sectional dimension of from about 5 micrometers (μm) to about 100 μm and a room temperature overall volume of from about 100 μm$^3$ to about 1000 μm$^3$, or even greater depending upon the size of the cell to be treated. Likewise, when considering retention of groups of cells (e.g., agglomerations, spheroids, organoids, etc.), the device can be designed with wells having appropriate dimensions for the cellular cluster, e.g. a room temperature largest cross-sectional dimension of about 100 μm or greater, such as about 500 μm or greater, about 1,000 μm or greater, about 2,000 μm or greater, about 3,000 μm or greater, about 4,000 μm or greater, or about 5,000 μm or greater in some embodiments, and a room temperature overall volume of about 500 μm$^3$ or greater, such as about 1,000 μm$^3$ or greater, about 2,000 μm$^3$ or greater, about 5,000 μm$^3$ or greater, about 10,000 μm$^3$ or greater, or about 100,000 μm$^3$ or greater in some embodiments.

To provide temperature responsive capability to the device, the well layer 12 includes a polymeric composition that comprises a thermoresponsive polymer. In general, any biocompatible thermoresponsive polymer can be utilized in forming the well layer, provided that the thermoresponsive polymer exhibits a critical solution temperature at or near a relevant temperature for a cell of interest and such that a deformation of the polymeric composite at the relevant temperature can cause a macroscopic variation in a geometry of the polymeric composition. Thermoresponsive polymers encompassed herein can include lower critical solution temperature (LCST) polymers, as well as upper critical solution temperature polymers (UCST), the critical solution temperature being that temperature at which a solution of the polymer will change from a single-phase system to a two-phase system. In one embodiment, a suitable thermoresponsive polymer can exhibit a critical solution temperature in a biologically relevant range; for instance, from about 20° C. to about 50° C. Of course, thermoresponsive polymers having a critical solution temperature outside of this range can alternatively be utilized; for instance, when considering utilization of a device for examination of the effects of mechanostimulation of cells at extreme temperatures, e.g., for examination of thermophiles, for examining cell activity at or near freezing temperatures, etc.

By way of example, and without limitation, thermoresponsive polymers as may be incorporated in a polymeric composition of a well layer of a device can include poly(N-isopropylacrylamide) (PNIPAM) having an LCST of about 32° C., poly(N,N-diethylacrylamide) (PDEAM) with an LCST of about 25° C. to about 32° C., poly(N-vinylcaprolactam) (PVCL) having an LCST between about 25° C. and about 35° C., and poly[2-(dimethylamino)ethyl methacrylate] (PDMAEMA) having an LCST of about 50° C., as well as combinations of thermoresponsive polymers. Moreover, modifications of thermoresponsive polymers as are known in the art can be utilized to adjust or fine-tune the thermoresponsive nature of the polymers. For instance, addition of or modification to side groups of a polymer, e.g., inclusion of a polyethylene glycol (PEG) side chain of 2-10 ethylene oxide units on a polymer backbone can decrease the critical solution temperature of thermoresponsive polymers.

The well layer 12 can generally include a polymeric composition that incorporates the thermoresponsive polymer in the form of a hydrogel. In general, the hydrogel can be a crosslinked hydrogel (i.e., in which at least a portion of the polymeric network is covalently crosslinked) that can incorporate a high quantity of water (e.g., up to about 99 wt. % water) without loss of structure over time.

In one embodiment, the well layer 12 can include a PNIPAM-based hydrogel. PNIPAM-based hydrogels have been extensively researched for biomedical applications. These hydrogels are of interest because the temperature-responsive properties can range between physiological (about 37° C.) and room (about 25° C.) temperatures. PNIPAM has a reversible LCST of about 32° C. allowing the hydrogel to exhibit an increase in volume when cooled from about 37° C. to about 25° C., thereby decreasing the volume of a well that is defined within a polymeric well layer 12, as illustrated in FIG. 1. Furthermore, a PNIPAM-based hydrogel can provide a platform for adherent cells.

While the polymeric composition of the well layer 12 can include one or more thermoresponsive homopolymers as the only type of polymer of the composition, in some embodiments, in order to better tune the characteristics of the layer and provide a suitable well volume change with temperature modification, the polymeric composition can include a thermoresponsive polymer in conjunction with a second polymeric component. The relative amount and type of the second polymeric component can be utilized to tune characteristics of the well layer such as mechanical strength of the layer, translucent properties of the layer, volume change characteristics of the layer, and thereby induced mechanical pressure on well contents, etc. For instance, a polymeric composite can incorporate a thermoresponsive polymer in an amount of from about 1 wt. % to about 99 wt. %, for instance from about 5 wt. % to about 50 wt. % in some embodiments, and can incorporate a second polymeric component in an amount of from about 1 wt. % to about 99 wt. %, for instance from about 50 wt. % to about 95 wt. %, in some embodiments.

In some embodiments, the second polymeric component can be a second polymeric network, and the well layer 12 can be in the form of an interpenetrating polymer network (IPN), in which two or more polymeric networks are physically entangled with one another. In some embodiments, distinct polymer types can interpenetrate one another, and chains of each polymer type can be maintained entangled but distinct (i.e., not covalently bonded) from chains of at least one other polymer type. In some embodiments, interaction between the different polymer types can together form a physical or crosslinked gel, e.g., polymers of different types can be crosslinked to one another such that the different polymer networks are covalently bonded to one another. In some embodiments, one or all of the polymer networks of the IPN (each polymer network being formed of a single type of polymer or copolymer) can be capable of forming a gel in their own right absent any other polymers. In some embodiments, one or more of the polymer types can be crosslinked to form a network of interstices, and one or more other polymer types can be distributed through the interstices of the network either with or without crosslinking of these polymers. For instance, in some embodiments, each of the polymer networks can be a crosslinked network, and the crosslinked networks can be physically entangled with one another.

In some embodiments, an IPN can be formed by initially polymerizing and crosslinking a first monomer. Thereafter, a second monomer can be disposed within the interstices formed upon the crosslinking of the polymerized first monomer. The second monomer can then be polymerized and optionally crosslinked, entangling the polymeric networks. In other embodiments, the monomers of the different polymers can be simultaneously polymerized, forming an interpenetrating network of two polymers, optionally in conjunction with crosslinking of one or more of the polymer types of the IPN, and further optionally by crosslinking the different polymer types to one another.

Examples of polymers as may be incorporated in an IPN in conjunction with a thermoresponsive polymer can include, without limitation, polyacrylamide, poly(ethylene glycol) diacrylate (PEGDA), polyacrylic acid, poly(hydroxyethyl methacrylate) (PHEMA), poly(ethylene glycol) (PEG), poly(vinyl alcohol) (PVA), poly(acrylic acid) (PAA), poly(methacrylic acid) (PMAA), as well as combinations of secondary polymers (i.e., polymers that are not thermoresponsive at all or not thermoresponsive at the temperatures of interest).

In one embodiment, a polymeric component can be copolymerized with a thermoresponsive polymer to provide a crosslinked hydrogel formed of the resulting thermoresponsive copolymer. By way of example, a monomer for forming a thermoresponsive polymer or a previously formed thermoresponsive polymer can be copolymerized with a second monomeric or polymeric component including, without limitation, butyl methacrylate (BuMA), hydroxyethyl methacrylate (HEMA), poly(dimethyl acrylamide) (PDMA), PEG, etc. The copolymer thus formed can be crosslinked to form a thermoresponsive hydrogel as described herein.

A polymeric composition that forms a well layer 12 can include additional components in conjunction with the polymer(s). For instance, in one embodiment, a polymeric composition that forms a well layer 12 can include an agent that can be expelled from the well layer 12 upon a volume change of the layer in response to a temperature change. An agent can be a biologically active agent that can be used for culturing a cell held within a well 14 of a well layer 12 or a cell held in conjunction with a device; for instance, adjacent to a device in a coculture application. In one embodiment, an agent can be a drug for delivery to cells or tissue held adjacent to a device; for instance, in a drug delivery application in which a well layer 12 can be a layer of a drug delivery patch, a stent, or the like.

Referring again to FIG. 1, in addition to the well layer 12, a thermoresponsive device can include a supporting base layer 10 that can provide strength and rigidity to the device, as well as to provide a static base for cells to rest upon that are contained in a well 14 of the device. In some embodiments, the supporting base layer 10 can be transparent or translucent, and as such, can allow for cell visualization, for example by use of transmission brightfield microscopy, e.g., as can be carried out to ensure adequate cell isolation.

In one embodiment, the supporting base layer 10 can be a hydrogel. In one particular embodiment, the supporting base layer 10 can include a polymer that is also present in the well layer 12, e.g., polymer that is not thermoresponsive at all or not thermoresponsive at the temperature range of interest. By way of example, a supporting base layer 10 can include a hydrogel of a polyacrylamide, poly(ethylene glycol) diacrylate (PEGDA), polyacrylic acid, poly(hydroxyethyl methacrylate) (PHEMA), poly(ethylene glycol) (PEG), poly(vinyl alcohol) (PVA), poly(acrylic acid) (PAA), poly(methacrylic acid) (PMAA), or combinations of polymers.

FIG. 2 illustrates one approach for forming a thermoresponsive device. As shown, in one embodiment, a formation approach can include initial formation of the supporting base layer 10. As illustrated in FIG. 2, a photopolymerization methodology can be utilized to form a device. According to this embodiment, a first precursor solution 11 can be applied in a layer-type orientation (e.g., by casting, spin coating, blade coating, etc.). The precursor solution 11 can include monomers, oligomers, or polymers that can be polymerized/crosslinked to form the base substrate layer 10. A precursor solution 11 can include other components as are generally known in the art as desired, which can be included for formation purposes, as well as for providing characteristics to the formed base substrate layer 10. For instance, a precursor solution 11 can include one or more of a photoinitiator, crosslinking agents, humectants, colorants, stabilizers, antimicrobials, etc., in conjunction with the polymer network-forming components (e.g., monomers) and a solvent.

In one embodiment, a precursor solution 11 can include a photoinitiator, e.g., a free-radical photoinitiation agent. Such photoinitiators are well known in the art and can generally be present in quantities of about 5 wt. % or less, for instance from about 0.02 wt. % to about 2 wt. %, or from about 0.02 wt. % to about 0.4 wt. %. In one embodiment, a photoinitiator can be type a-hydroxy-ketones or a benzilidimethylketal. Exemplary photoinitiators can include, without limitation, dimethoxybenzylphenone (Irgacure® 651 from Ciba Specialty Chemicals), 2-hydroxy-2-methyl-propiophenone (Daracur® 1173 from Ciba Specialty Chemicals), I-hydroxycyclohexylphenylketone (Irgacure® 184 from Ciba Specialty Chemicals), diethoxyacetophenone, 4-(2-hydroxyethoxy)phenyl-(2-hydroxy-2-methylpropyl) ketone (Irgacure® 2959 from Ciba Specialty Chemicals), or any combination of photoinitiators.

In some embodiments, a precursor solution can include a polyfunctional crosslinking reagent capable of reacting with functional groups of a polymer. Typical crosslinking agents can include ethyleneglycol diglycidyl ether, polyols such as glycerol, and other polyfunctional reagents known to the art. Examples of polyfunctional monomeric crosslinkers include, without limitation, polyethyleneoxide di(meth) acrylates with varying PEG molecular weights, trimethylolpropane ethoxylate tri(meth)acrylate with varying ethyleneoxide molecular weights, trimethylolpropane tri(meth) acrylate, divinylbenzene, pentaerythritol triacrylate, pentaerythritol triallyl ether, triallylamine, N,N-methylene-bis-acrylamide, and combinations thereof.

A precursor solution 11 can include other common additives known in the art such as, and without limitation to, polymerization inhibitors, chain transfer agents, salts, surfactants, buffers, preservatives, antioxidants, pigments, humectants, and the like. In general, additives can be present in a precursor solution in an amount of about 10 wt. % or less for each additive; for instance, about 5 wt. % or less, or up to about 3 wt. %.

To affect polymerization of a precursor solution 11, incident radiation, e.g., ultraviolet (UV) radiation, can be directed at the precursor solution 11. Incident UV intensity can typically be at a wavelength in the range from about 240 to about 400 nm and can overlap to at least some degree with the UV absorption band of a photoinitiator. The incident light can be directed at the precursor solution 11 at sufficient intensity and exposure duration (e.g., about 3000 mW/cm$^2$) to activate the polymerization in a reasonable time, e.g., on the order of a few minutes, and form the base substrate layer 10.

The well layer 12 can then be formed on a surface of a supporting base layer 10 by polymerizing components of a second precursor solution 13. The second precursor solution can include monomeric or polymeric components, as well as additives as discussed above. In some embodiments, a second precursor solution 13 can include a biologically active agent for delivery from the well layer 12. For instance, a second precursor solution 13 can include a drug or cell culturing agent for delivery to cells held within the wells of a device or to cells or tissue held adjacent a device. In addition to other components, the precursor solution 13 will include monomeric or polymeric components of the thermoresponsive polymer of choice. For instance, a precursor solution 13 can include a first polymeric component for formation of the thermoresponsive polymer network of a well layer, e.g., monomers or polymers of a thermoresponsive polymer network, as well as a second polymeric component for formation of a secondary polymer network of an IPN, e.g., monomers or polymers of a secondary polymer network, that is not thermoresponsive at the relevant temperatures of use for the thermoresponsive device to be formed. Upon effecting the polymerization reaction of the precursor solution 13 through addition of energy (e.g., UV photopolymerization), a well layer 12 including the polymeric composition can be formed that includes the thermoresponsive polymer of choice and that encapsulates any additives of choice.

Wells 14 can be formed in the well layer 12 either in conjunction with the polymerization of the precursor solution 13 or following formation of the polymeric composition. For instance, the wells 14 can be formed in conjunction with the polymerization by utilizing a photomask 15 that can mask a portion of the precursor solution 13 and prevent polymerization in those masked areas. As indicated in FIG. 2, following polymerization, the photomask 15 can be removed as can the precursor solution 13 from the masked areas, leaving the wells 14 defined within the well layer 12.

Alternatively, the wells 14 can be formed by removal of polymeric composition from the areas desired for the wells 14 following polymerization. For instance, a continuous well layer 12 can be etched or otherwise treated to remove the polymerized material from the desired areas and form the wells 14 within the well layer 12.

Figure 11:
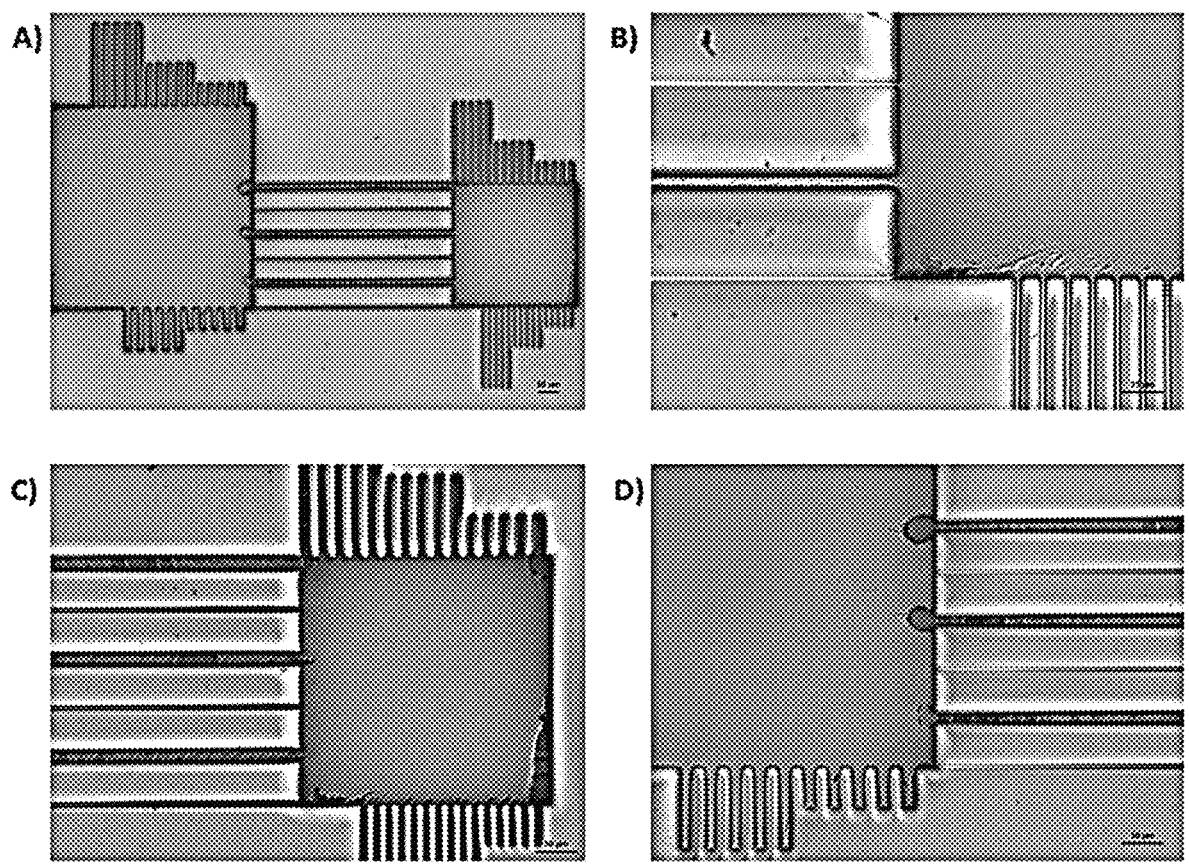
FIG. 11 presents brightfield microscopy images of a cell culture medium as described having a microfluidic pattern taken at A) 10×, C, D) 20×, and B) 40× magnifications.

Beneficially, formation techniques can provide the thermoresponsive well layer 12 including wells 14 of various shapes and sizes that can encapsulate and systematically apply mechanical pressure on materials (e.g., cells) held within the wells 14. The well layer 12 provides a mechanism for induction of rapid mechanical pressure to contents of the wells 14, as it includes a thermoresponsive component in the polymeric composition of the layer 12. By way of example, and without limitation, wells can be formed to have a cross-section in the form of a circle, a square, a rectangle, a triangle, any other regular or irregular polygon, a star, a letter ('Y', a 'T', an 'L', an 'H') that can include straight or curved sections (e.g., a deformed letter), etc. In one embodiment, a device can include wells that include chambers and/or channels. For instance, a well can include multiple chambers of any desired shape and the chambers can be connected via channels. One example of such a device is illustrated in FIG. 11. Upon mechanical stimulation, cells or other content retained in such a well can be forced into or out of an area of the well. For instance, temperature-controlled mechanical stimulation can force content into or out of channels of the well and can be used to push content (e.g., cells or culture agents) from one chamber to another.

FIG. 1 illustrates a cell deformation mechanism as can be instigated by use of disclosed devices. As indicated, a single cell 18 encapsulated in a microwell 14 can be mechanically deformed upon a temperature-controlled increase in volume of the well layer 12, and a corresponding decrease in volume of a well 14. Beneficially, the degree of mechanical pressure induced by the temperature modification can be tunable through design of the well shape and size, as well as through design of the polymeric composition used to form the well layer 12. For instance, the ratios of the different polymer types used in forming an IPN can be adjusted to control the volume modification characteristic with temperature change, which can control the degree of mechanical pressure induced on the encapsulated cells. As indicated in FIG. 1, upon the temperature-controlled volume modification of the well layer 12, a single cell 18 encapsulated in a well 14 can be mechanically deformed. This mechanical deformation of the cell can cause membrane disruption, which can allow the bi-directional diffusion of agents into and out of the cytoplasm of the cell 18.

During use, a device can be incubated with cell media. Following, single cells, cell clusters, cell spheroids, or organoids can be encapsulated within individual microwells; for instance, via a wiping process, injection, etc. Upon modification in temperature of the well layer 12, the microwells can quickly change in size, inducing a mechanical pressure on the encapsulated cell(s). As discussed previously, either homogenous or heterogenous mechanical pressure can be induced on the cells depending upon on the selected microwell geometry. The mechanical pressure can then be stopped or paused by again modifying the temperature of the well layer 12 by either heating or cooling, depending upon the nature of the thermoresponsive polymer.

Mechanical pressure induced on encapsulated cells can provide two primary effects: the first, being to create transient holes in the cell membrane allowing either intracellular delivery of targeted agents or excretion of intracellular components; the second, being to mechanically-stimulate cells for specified durations. Disclosed devices can be used in a wide variety of applications that can take advantage of one or both of these effects. For example, cellular engineering relies on intracellular component co-localization and restructuring upon cellular deformations, which may lead to significant phenotypic changes within the cell depending on the cell type and degree of mechanical deformation; (multipotent) cardiac stem cells are an example of these cells, where mechanical stimuli lead to significant downstream effects (i.e., differentiation). Diagnosis of phenotypic (or genotypic, in the instance of cancer) properties by use of disclosed systems can utilize the observation or measurement of cellular responses (i.e., deformational resistance, creep, elasticity, secretion, intracellular restructuring) upon or after cellular deformation.

Disclosed systems can be used in a variety of applications as would be evident to one of ordinary skill in the art. By way of example, in one embodiment, a device can be utilized for delivery of agents into encapsulated cells, e.g., high-throughput delivery/transport of biological (i.e., DNA, RNA, proteins, lipids, carbohydrates, cytokines, chemokines, natural compounds) or non-biological (i.e., nanoparticles, quantum dots, synthetic compounds) agents into the encapsulated cells, cell clusters, cell spheroids, or organoids.

Disclosed devices provide a non-viral platform that is able to increase delivery efficiency through the means of mechanical cellular deformation. Intracellular delivery of various normally-impermeable, bioactive agents, especially large, charged, and polar agents, is of great interest for various therapeutic and research techniques. Agents to be delivered can be located in the wells as a component of a cell culture media or can be encapsulated within the well layer 12 during formation. Examples of such agents can include, without limitation, nucleotides, nanoparticles, quantum dots, and proteins for immunotherapy therapy and intracellular labeling among other uses. In immunotherapy therapy, effective intracellular delivery of virus-/cancer-specific antigens to antigen-presenting cells (APCs) has been highly sought after. APCs are cells that present antigens on their surface through major histocompatibility complexes (MHCs), which activate endogenous T-cell responses for attacking viruses and tumors. Although current intracellular delivery techniques, such as electroporation, sonoporation, the use of polymeric nanoparticles, liposomes, and chemical modifications of the agents, have been employed in both therapeutic and research settings, these techniques have been inefficient due to low cell viability, agent trapping in endosomal vesicles, undesirable chemical modifications to the agent, and damage to the agent.

The thermoresponsive devices can be used as a vector-free method for gene transfection due to the ability to create transient holes in the cell membrane, allowing increased diffusion through the membrane. As such, genetic material can enter the cell via diffusion. Transfection is most commonly performed to express a protein of interest in cultured cells (or an animal model) through the use of a plasmid vector or mRNA. Expression of the protein in eukaryotic cells allows the recombinant protein to be produced with proper folding and post-translational modifications required for its function. Further, introducing proteins with readily detectable markers and other modifications into cells allows the study of promoter and enhancer sequences or protein: protein interactions. In addition, transfection can be used in various forms of bioproduction depending upon the transfection strategy. For example, delivery of reprogramming transcription factors enables the generation of induced pluripotent stem cell (iPSC). Stable transfection, on the other hand, provides the means for the bioproduction of various therapeutic molecules. The temperature responsive devices can be used to rapidly screen drug panels on various cell types with mechanical cell deformation, allowing increased drug uptake.

In one embodiment, a temperature responsive device can be employed as a "smart" drug-delivery device that is able to utilize temperature as an environmental stimulus and release a pharmacological agent based on the surrounding temperature. For instance, a device can be in the form of a topical patch that can rapidly release a pharmacological agent to a tissue surface once applied. Drug applications can include wound healing, viral transfection, and immunotherapy (e.g., in treatment of vitiligo). The patterning of the wells of a device can allows for a heterogenous distribution of a drug, which may be sought depending on the specific therapeutic application.

In such an embodiment, a thermoresponsive device can be utilized to release contents from a well 14 in response to a temperature change. For instance, a device can be located on a surface containing cells, e.g., a device in the form of a patch can be located on a skin surface. Upon a change in temperature, the temperature change and related volume change of the wells 14 can expel the contents held in the wells 14 of the device, and thereby deliver the agent to the surface. In another embodiment, in which an agent can be encapsulated in the polymeric composition that forms the wells, a change in temperature can lead to a release of the agent from the polymeric composition, and the agent can be delivered either to cells retained within the wells or to cells adjacent to the device; for instance, in a co-culture or drug delivery application.

In another embodiment, a device can be used for in vitro drug screening, in which an agent can be introduced to one or more cells retained in a device. Following, a mechanical strain can be introduced to the one or more cells in the presence of the agent, and a determination can be made as to whether or not the agent has bioactivity with respect to the one or more cells under the mechanical strain.

The devices can also be used to determine the production of a compound by a cell. For instance, a coating can be applied to a surface of the wells, and the coating can include a binding substance having the ability to bind a substance produced by a target cell (e.g., a specific binding member or the like). Upon culturing cells in the device in a state that permits the diffusion of the substance of interest out of the cells and into the wells, the presence of the substance at the coating layer can be determined; for instance, by use of a detectable label that can be a component of the coating layer or that can be added to the wells following the diffusion of the substance from the cells (and optional removal of the cells from the wells).

In one embodiment, a temperature responsive device can apply sustained mechanical pressure in order increase cellular secretion by means of diffusion across the cellular membrane. The cellular secretion is known as the secretome of the cell and its study can lead to the discovery of previously unknown, potentially therapeutic or diagnostic, targets. The secreted proteins in humans account for 13-20% of the entire proteome and include growth factors, chemokines, cytokines, adhesion molecules, proteases, and shed receptors. Human protein-coding genes (39%, 19613 genes) are predicted to have either a signal peptide and/or at least one transmembrane region suggesting active transport of the corresponding protein out of the cell (secretion) or location in one of the numerous membrane systems in the cell. Increasing evidence showed that, in addition to the protein cargo, non-protein components, such as lipid, micro-RNAs, and messenger-RNA, could also be secreted by cells via both microvesicles (100→1000 nm diameter)—shedding from the plasma membrane—and exosomes (30-150 nm diameter)—released via endosomal-exocytosis event. Factors present in both these organelles accounts for up to 42% of the secretome and have been incorporated as the collective secretome.

As an example of such an application, a temperature responsive device can be used to mechanically squeeze B cells in order to increase the secretion of soluble antibodies and chemokines into the extracellular environment. As another example, a device can be used to deform *E. coli* cells in order to increase the secretion of proteins into the extracellular environment. In one embodiment, the device can be utilized to deliver the secreted materials to the surrounding area. For instance, the device can be in the form of a patch that can be held adjacent to a subject, and materials secreted from the cells upon the temperature change can be delivered to the subject in a drug delivery application, e.g., for immunotherapy. In another embodiment, such an approach can be used in an in vitro application; for instance, in investigation or engineering of cells in the presence of controlled cellular secretions from near-by cells held in the device, for instance, in a co-culture system.

Mechanical pressure on encapsulated cells can be utilized to assess and correlate cellular response/properties (i.e., membrane mechanics, organelle co-localization), which can be used in one embodiment to diagnose cell type and properties. In the context of cancer diagnostics, this platform can be used for predicting the invasiveness or metastatic potential of a cancer cell comprising: (a) determining the creep compliance (deformability) or the spring constant (stiffness) of the cancer cell; and (b) predicting the invasiveness or metastatic potential of the cancer cell based on the determination of step (a), wherein the creep compliance of the cell is proportional to the invasiveness and the metastatic potential of the cell and the spring constant is inversely proportional to the invasiveness and the metastatic potential of the cell. For example, devices can be used for screening for an agent capable of reducing the invasiveness of a cancer cell by contacting the cancer cell with the agent and determining the creep compliance or spring constant of the cell after contact with the agent, wherein an agent capable of decreasing the creep compliance or increasing the spring constant of the cell as compared to a second cancer cell not contacted with the agent can be determined to be an agent capable of reducing the invasiveness of the cancer cell. In another determination of the creep compliance (deformability) or the spring constant (stiffness) of a cell from a subject can be used to predict whether the cell is cancerous, as a high creep compliance can be predictive of the cell being cancerous and a low spring constant can be predictive of the cell being cancerous.

A device can be used to encapsulate individual cells for the purposes of assessing the proliferative potential of each cell, especially under continuous or cyclical mechanical loading. The isolation of a single cell can allow for the accurate assessment of fold expansion and cellular generations stemming from the initial cell. Extracting mechanical properties of the cell from cell deformation behavior and cell response to the compression force.

In yet another embodiment, devices can be used to control cell surface topography in order to accurately assess membrane diffusion. The process of cellular deformation serves to restructure the cellular geometry and provides a rounding-smoothing effect of the apical cell surface allowing a more homogenous membrane topography to accurately assess membrane diffusion kinetics. It is known that the cellular membrane varies vastly between cell types. However, little is known how exactly topography-independent membrane diffusions differ, as no current methods allow for the elimination of the membrane topography variable.

Devices can also be used to assess actin polymerization and restructuring. Many aspects of cellular physiology rely on the ability to control mechanical forces across the cell. For example, cells must be able to maintain their shape when subjected to external shear stresses, such as forces exerted by blood flow in the vasculature. During cell migration and division, forces generated within the cell are required to drive morphogenic changes with extremely high spatial and temporal precision. Moreover, adherent cells also generate force on their surrounding environment; cellular force generation is required in remodeling of extracellular matrix and tissue morphogenesis. This varied mechanical behavior of cells is determined, to a large degree, by networks of filamentous proteins called the cytoskeleton. Although tools exist to identify the proteins in these cytoskeletal networks and to study their structure and their biochemical and biophysical properties, an understanding of the biophysical properties of dynamic, multiprotein assemblies is still lacking.

Disclosed devices can also be useful in cellular engineering applications. For instance, a device can be used to mechanically and cyclically stimulate cardiac cells in order to mimic physiological heart contractions. After mechanostimulation, cardiac adipose tissue-derived progenitor cells (ATDPCs) increase the expression of structural genes and there is a rising trend on cardiac transcription factors. Biophysical cues can be sensed and transduced into intracellular responses to regulate downstream gene expression and stem cell fate; a process known as mechanotransduction. In addition, mechanical forces can directly regulate the cell fate through modulating calcium signals. On one hand, mechanical stress activates stretch-activated channels, which causes cytoskeletal remodeling and regulates cell proliferation. On the other hand, mechanical stress on cells attached to the ECM induces integrin rearrangement, and the subsequent differentiation response. Wnt and MAPK signaling pathways are the most frequent; however, others have been described to regulate stem cell differentiation, such as TGF-β1, Notch, Smad, and Hedgehog signaling pathways. Taken together, mechanical stimuli affect both proliferation and differentiation, and although the complete scheme with all molecular pathways involved remains to be elucidated, disclosed devices can provide a route to such understandings.

Mechanostimulated cardiac ATDPCs grown on vertical surfaces also differentially expressed proteins that regulated the immune response (complement C3 protein), ECM assembly/disassembly (tissue inhibitor of metalloproteinase 1 [TIMP-1], vimentin, and collagen type VI α-1 chain), angiogenesis (fibronectin [FN]), and cell adhesion (FN, collagen type VI α-1 chain). Mechanostimulated cardiac ATDPCs grown on smooth surfaces also differentially expressed proteins involved in ECM assembly/disassembly (TIMP-1, matrix metalloproteinase 2 [MMP-2], collagen type VI α-1 chain), angiogenesis (MMP-2), immune response (pentraxin-related protein 3 [PTX3]), cardiomyogenesis and proliferation (follistatin-related protein 1 [FSTL1]), and cell adhesion (collagen type VI α-1 chain). Mechanostimulated subcutaneous ATDPCs seeded on horizontal surfaces also express proteins for ECM assembly/disassembly (α-2-macroglobulin [α-2-M]), transcription regulation and cell proliferation (Thioredoxin [TXN]), and cell adhesion (collagen type VI α-1 chain). Disclosed devices can be utilized to increase understanding of such systems.

As devices can be utilized to induce cyclic mechanical deformations on cell clusters/sheets for the formation of cell spheroids, devices can be utilized in study of both formation of spheroids as well as in screening for compounds that inhibit formation of spheroids.

Cell types as may be examined by use of the devices are not limited. For instance, a device can be used to mechanically activate T cells, dendritic cells, cancer cells, cardiac cells, muscle cells, stem cells, differentiated stem cells, etc., as well as adherent cells or nonadherent cells. For instance, a device can be used to constrain non-adherent cells in order to examine or assess a single region or surface. Non-adherent cells are usually retained in suspension, which causes difficulty in mechano-manipulation. This difficulty can be overcome by disclosed devices. For example, microwell constrained cells can be easily probed (i.e., needle injection for in-vitro fertilization). Current in-vitro fertilization (IVF) methods require the use of a suctioning pipette in order to constrain the ovum; such methods risk damage to the ovum due to concentrated pressure gradients on the cell membrane.

The present disclosure may be better understood with reference to the Examples set forth below.

EXAMPLE

Polyethylene glycol diacrylate (PEGDA), N-Isopropylacrylamide 97% (NIPIAM), N,N'-Methylenebis(acrylamide) 99% (BIS), potassium persulfate ≥99.0% (KPS), Irgacure® 2595, and 2-hydroxy-2-methylpropiophenone were purchased from Sigma-Aldrich. MDA-MB-231 cells were obtained from ATCC (Manassas, VA). A long wave ultraviolet (UV) lamp (365 nm wavelength) model B 100 YP was purchased from UVP. A custom photomask was purchased from JD Photo-Tools (Manchester, UK). A 2.5 mm-thick silicon sheet and a polyethylene terephthalate (PET) film were purchased from VWR. All chemicals were used as supplied without further purification.

Figure 3:
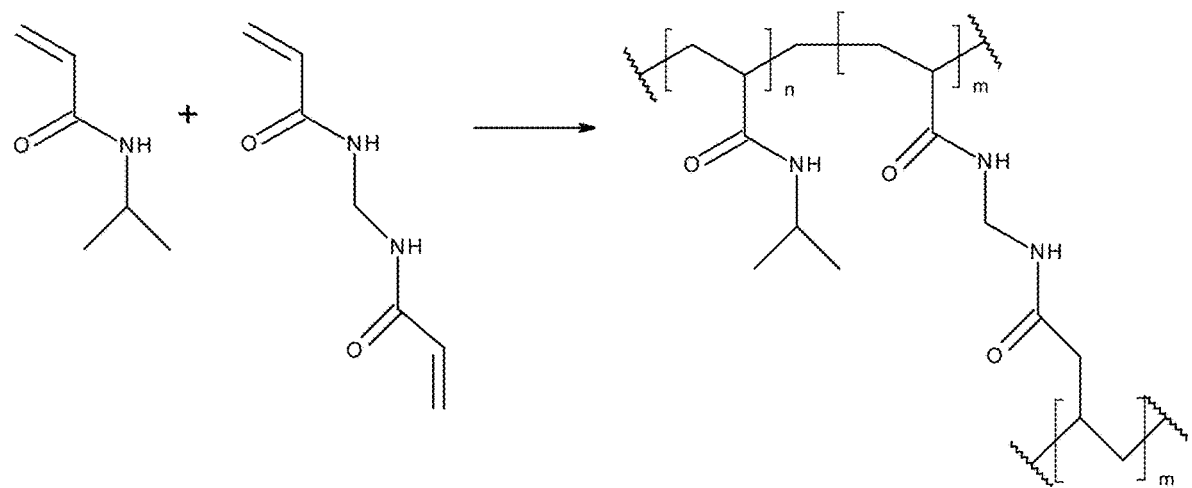
FIG. 3 provides a reaction scheme for formation of a thermoresponsive polymer as may be utilized in a thermoresponsive device as described herein.

To create the mold for the hydrogel, a 20 mm diameter circle was removed from a silicon sheet using a biopsy punch. The silicon sheet with the hole was then glued to a transparent PET sheet. To create the UV-photocrosslinkable precursor solution for the base hydrogel, a solution of 30% (v/v) PEGDA, 70% (v/v) water, and 0.5% (v/v) photoinitiator 2-hydroxy-2-methyl propiophenone was created. To create the UV-photocrosslinkable thermoresponsive precursor solution, a solution containing 7% (w/v) NIPAM, 2% (w/v) BIS, 0.05% (w/v) KPS, and 1% (w/v) Irgacure® 2595 was mixed with a solution containing 30% (v/v) PEGDA, 70% (v/v) water, and 0.5% (v/v) photoinitiator 2-hydroxy-2-methyl propiophenone in a 1:1 ratio. The PNIPAM polymerization reaction between the NIPAM and BIS monomers is illustrated in FIG. 3. The PEGDA-PNIPAM solution was bubbled with $N_2$ gas to purge the solution of oxygen and kept in an ice bath until use.

To create the base hydrogel, 500 μL of the UV-photocrosslinkable PEGDA solution was pipetted into the silicon/PET μL mold, making sure there were no air bubbles in the solution. The PEGDA precursor solution was then irradiated with UV light for 1 minute. To create the PEGDA-PNIPAM microwells, 200 μL of the UV-photocrosslinkable PEGDA-PNIPAM solution was pipetted onto the base PEGDA hydrogel while still in the silicon mold. A photomask was aligned on top of the solution making sure the solution was in full contact with the photomasks and that there were no air bubbles. As schematically illustrated in FIG. 3, the solution was irradiated with UV light for 45 seconds. The resulting hydrogel was removed from the silicon mold and the photomask and washed with and placed in DI water.

Figure 4:
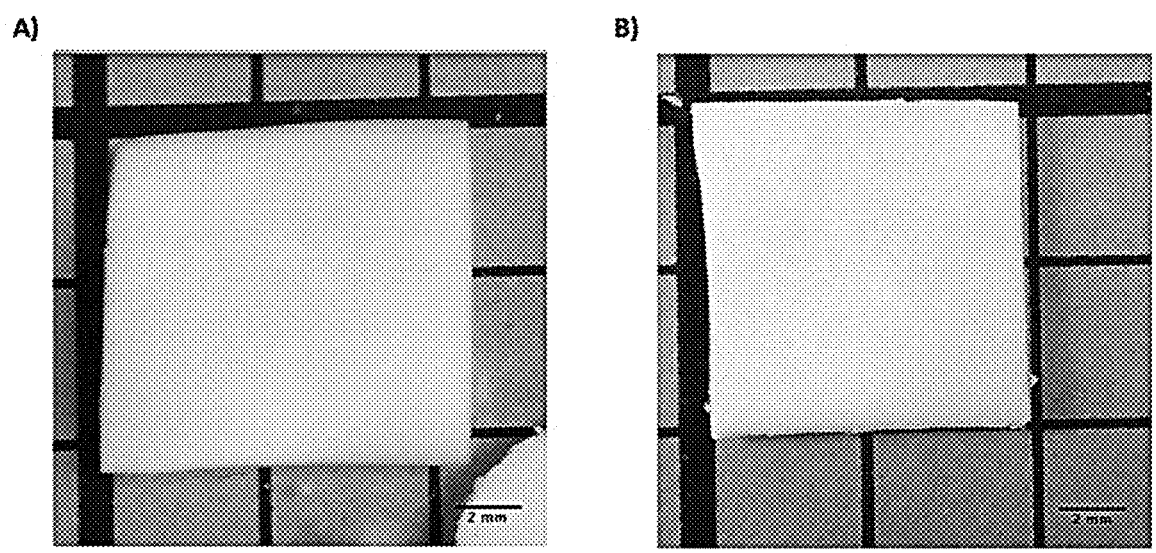
FIG. 4 presents macroscopic images of a thermoresponsive hydrogel at room temperature (25° C.) at A) and at physiological temperature (37° C.) at B) and shows the change and resulting modification in size.
Figure 5:
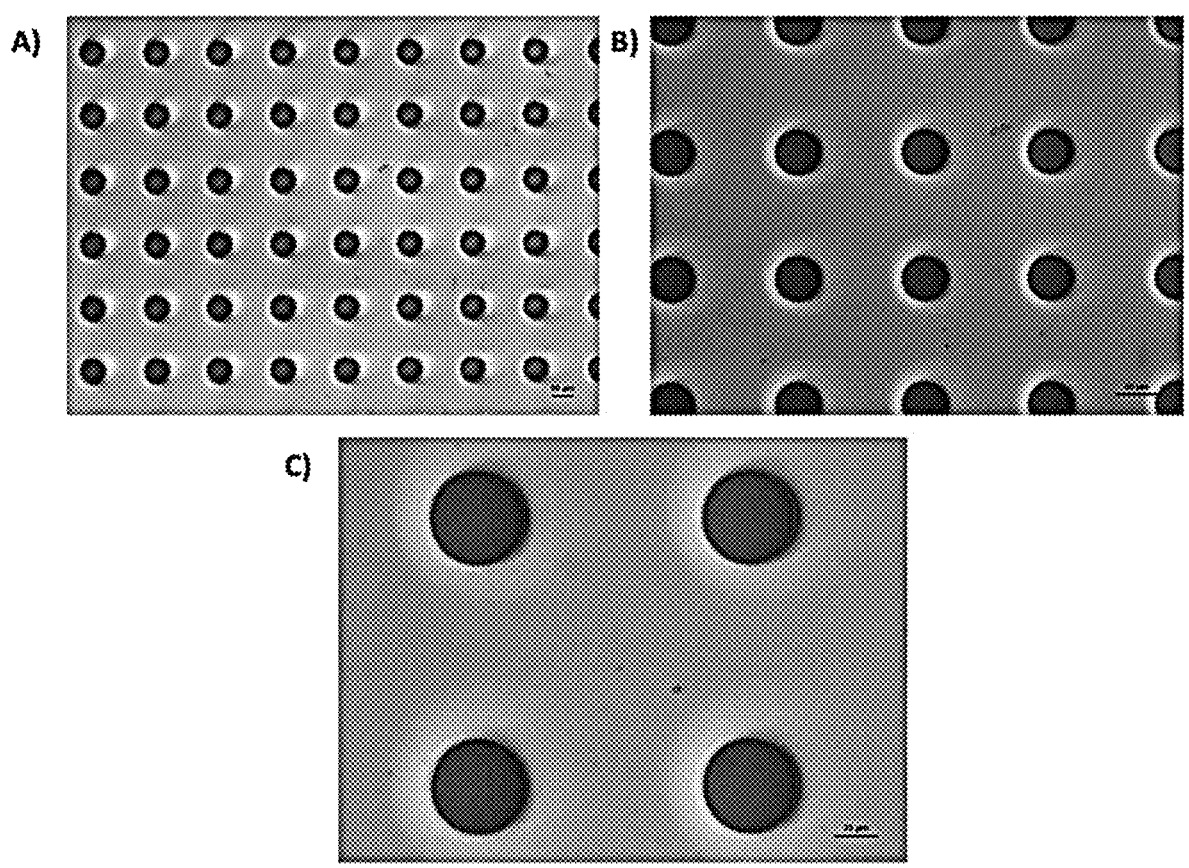
FIG. 5 presents brightfield microscopy images of microwells having a circular cross-section taken at A) 10×, B) 20×, and C) 40× magnifications.
Figure 6:
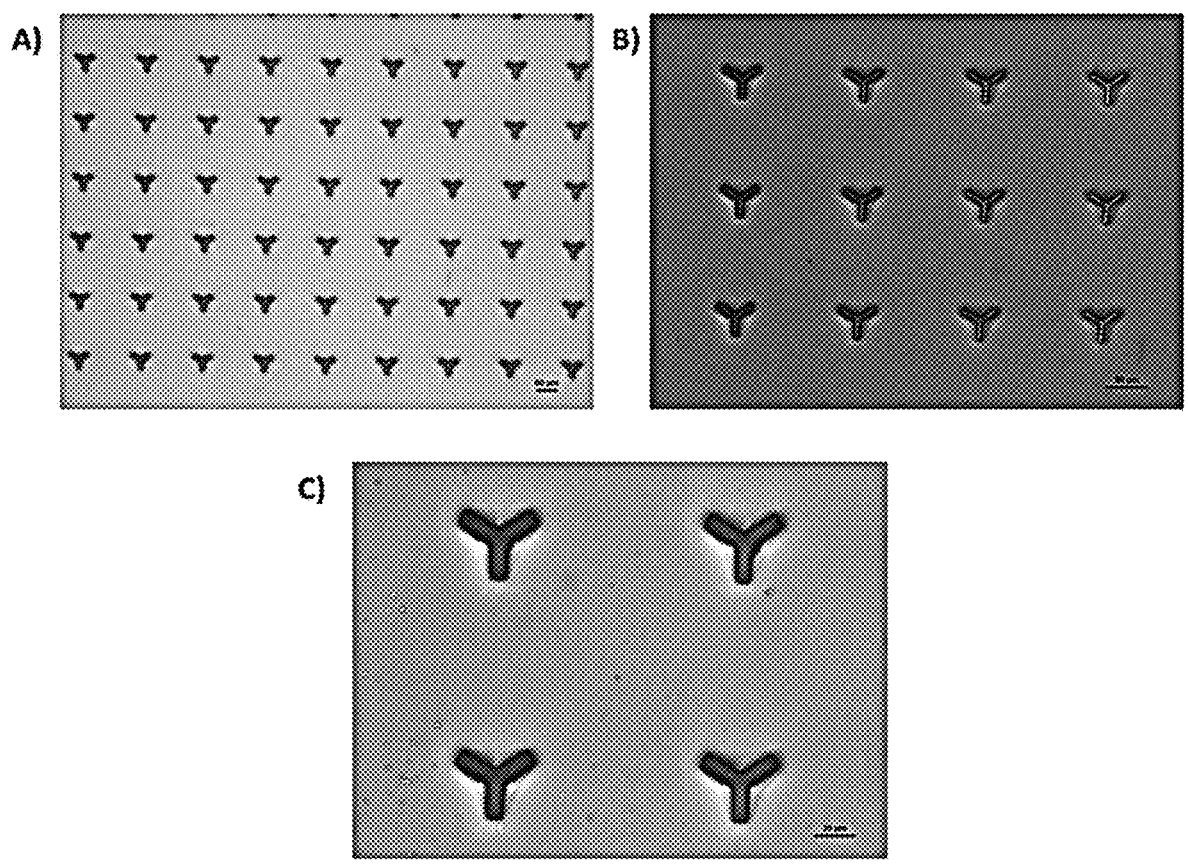
FIG. 6 presents brightfield microscopy images of microwells having a 'Y' cross-section taken at A) 10×, B) 20×, and C) 40× magnifications.
Figure 7:
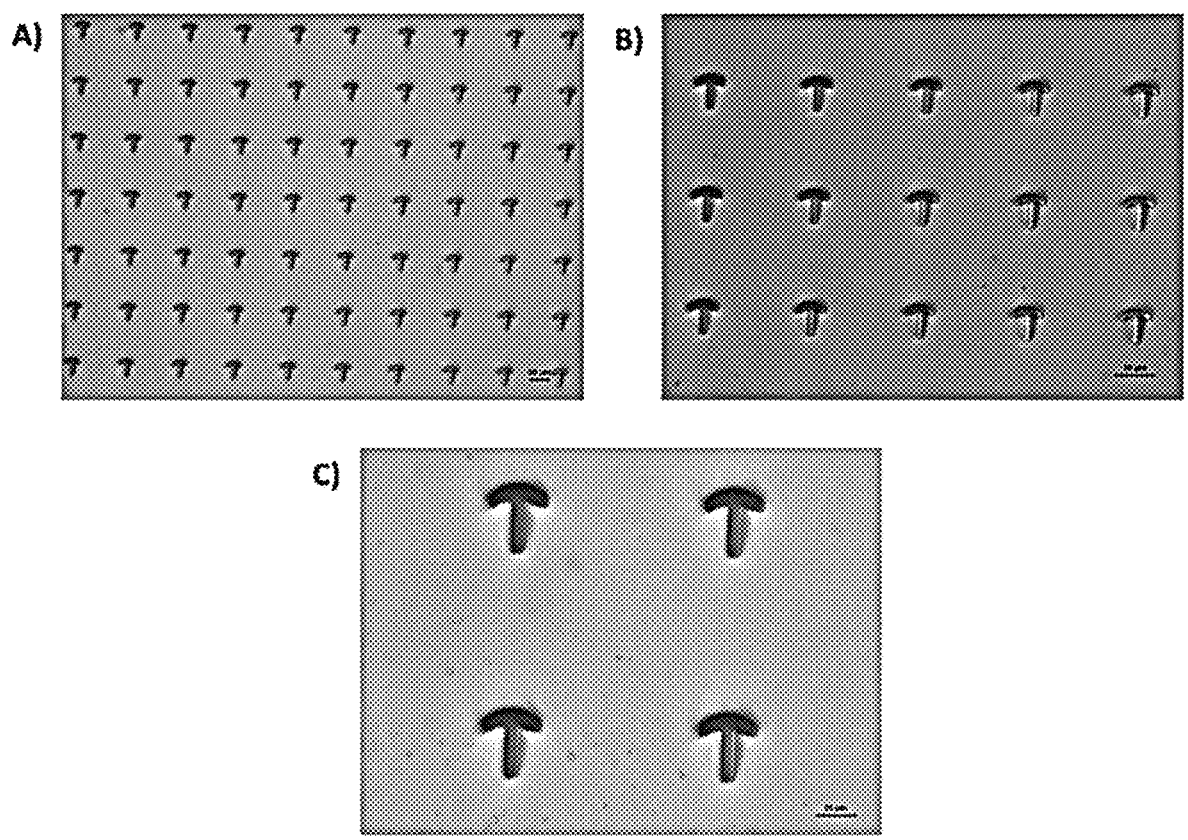
FIG. 7 presents brightfield microscopy images of microwells having a CT' cross-section taken at A) 10×, B) 20×, and C) 40× magnifications.
Figure 8:
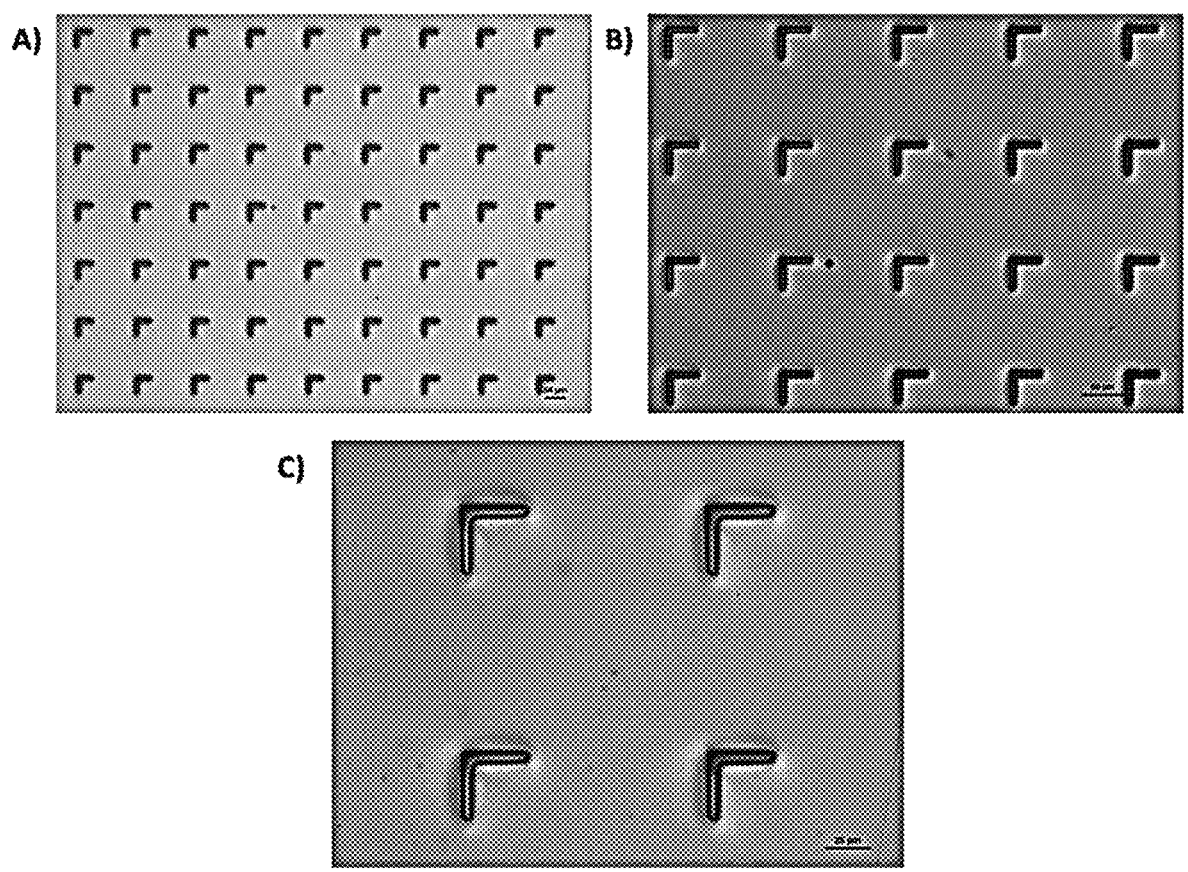
FIG. 8 presents brightfield microscopy images of microwells having an cross-section taken at A) 10×, B) 20×, and C) 40× magnifications.
Figure 9:
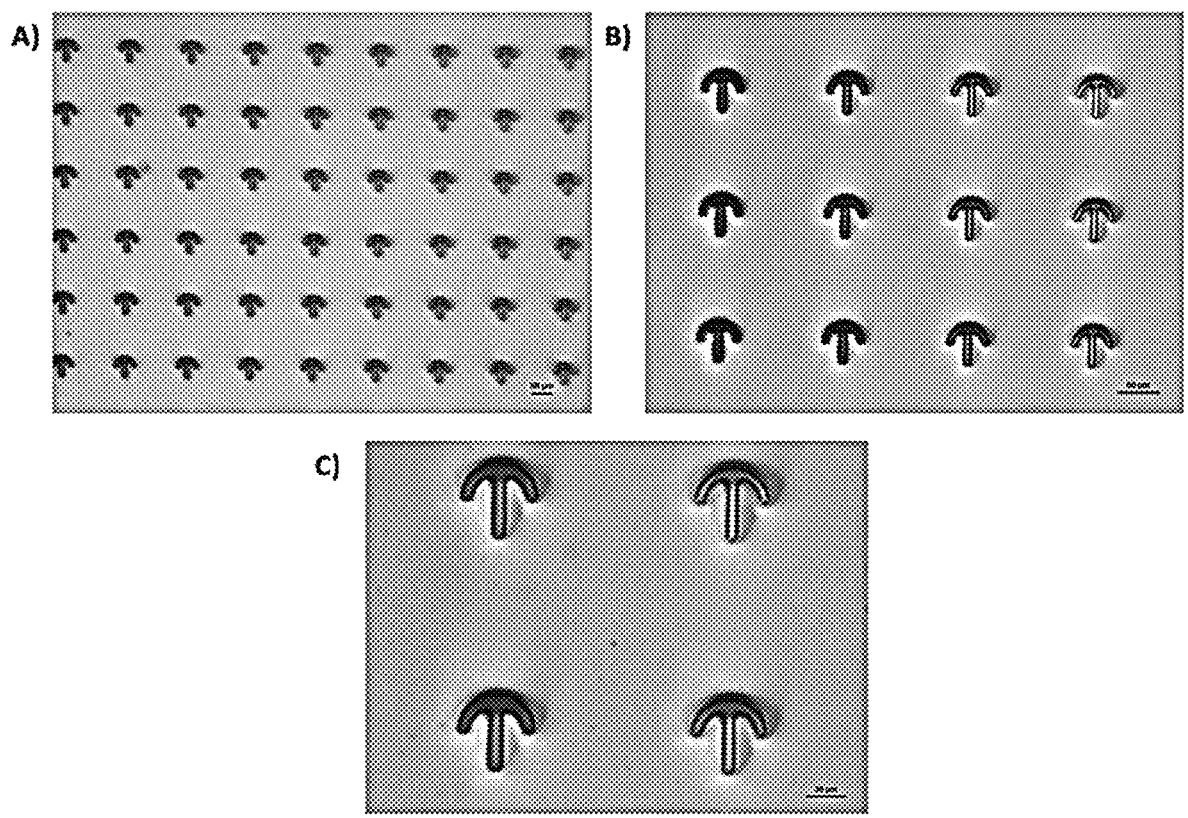
FIG. 9 presents brightfield microscopy images of microwells having a modified 'T' shaped cross-section taken at A) 10×, B) 20×, and C) 40× magnifications.

To remove unreacted compounds, the hydrogel underwent a thermocycling process which utilized the hydrogel's temperature-dependent swelling/de-swelling characteristics to maximize removal of uncrosslinked compounds. The thermocycling process involved: 1) submerging in 60° C. water for 10 minutes; 2) decanting and rinsing twice with DI water; 3) submerging in DI water ice bath for 20 minutes; and 4) warming to room temperature. The thermocycling process was performed for a total of 3 repetitions. FIG. 4 demonstrates, on a macroscopic level, the temperature dependent swelling properties of a typical hydrogel.

Figure 10:
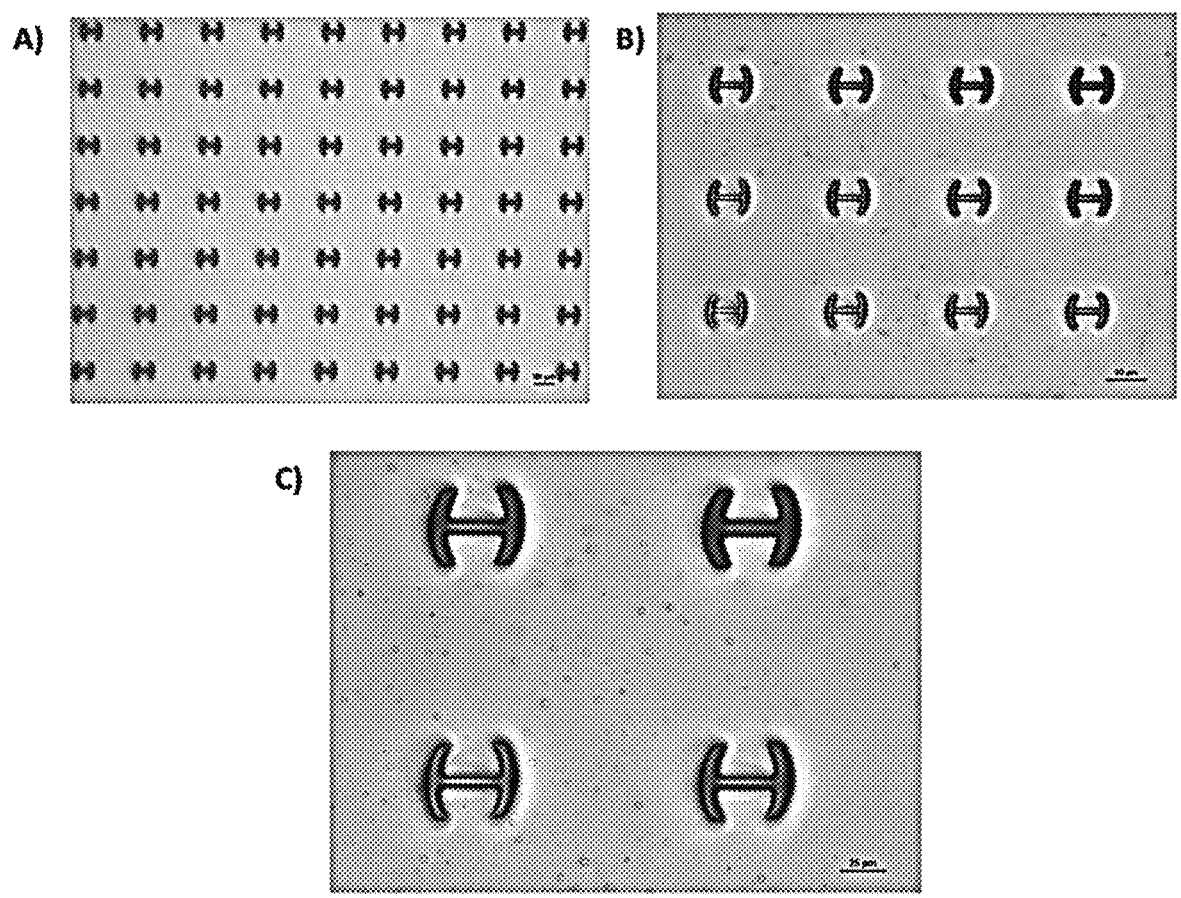
FIG. 10 presents brightfield microscopy images of microwells having a rounded 'H' shaped cross-section taken at A) 10×, B) 20×, and C) 40× magnifications.

Several different microwells shapes were fabricated on PEGDA-PNIPAM hydrogels including 'T', 'Y,' horseshoe-shaped, bell-shaped, circle, and microfluidic patterns, examples of which are illustrated in FIG. 5-14 including microwells having a circular cross-section (FIG. 5), a 'Y' cross-section (FIG. 6), a 'T' cross-section (FIG. 7), an cross-section (FIG. 8), a horseshoe-shaped cross-section (FIG. 9), and a bell-shaped cross-section (FIG. 10). FIG. 11 illustrates a cell platform in which the design is a microfluidic pattern including channels of various sizes, for instance, as may be used in cell sorting.

Brightfield images were used to quantify the average microwell size. Two methods within ImageJ were employed: manual and computational measurements. The "Find Edges" function was used to highlight the walls of the microwells. The measure tool was used to manually measure the diameters of each microwell. The "subtract background" and "enhance contrast" options were selected to allow the microwells to be more apparent. The color balance was adjusted to identify the microwell boundaries and the "analyze particles" function was used to computationally determine the size of the microwells.

Figure 12:
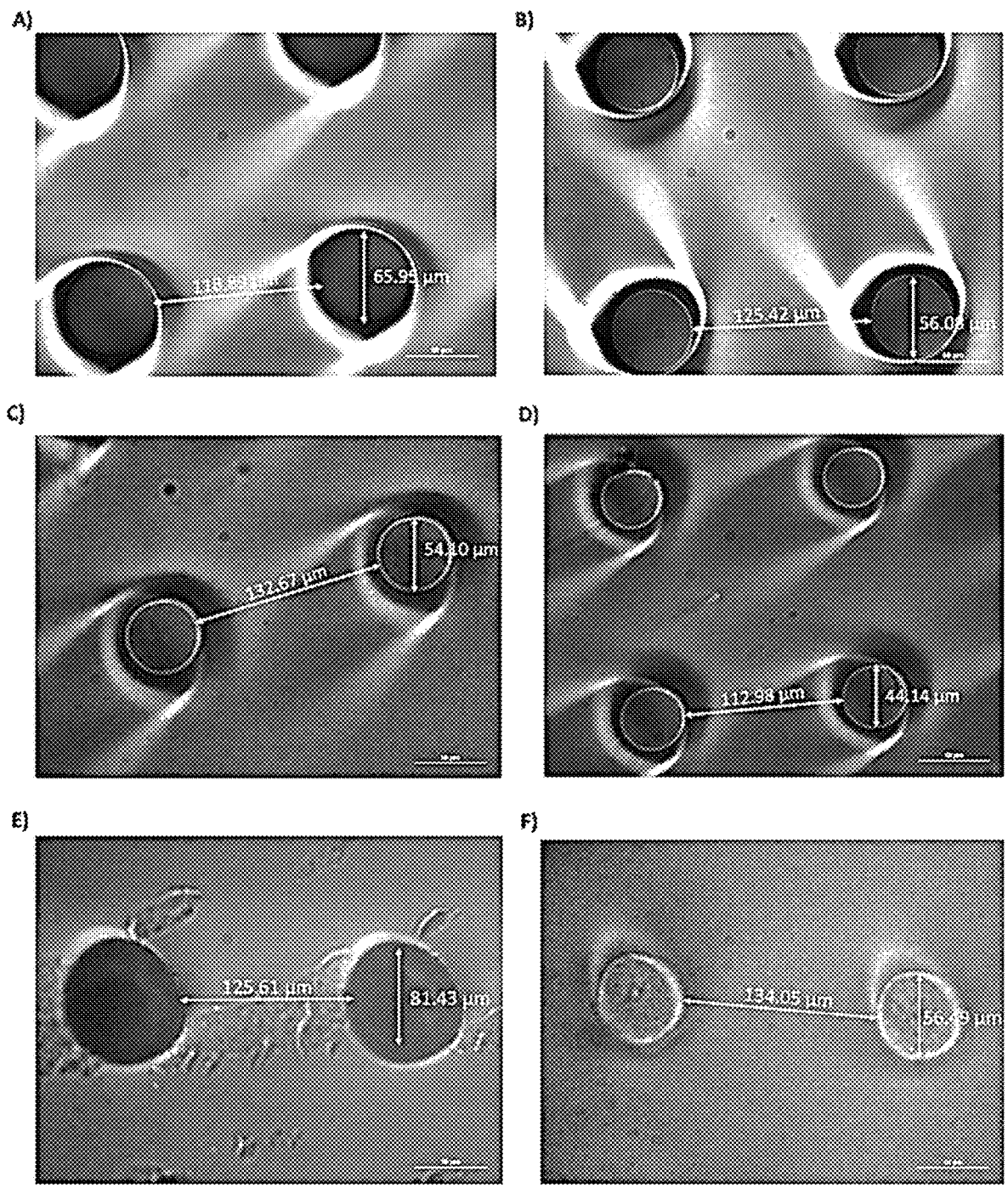
FIG. 12 illustrates microwells having a circular cross-section at different temperatures. The microwells are shown with measurements as indicated at 37° C. (A, C, E) and at 25° C. (B, D, F). All images were taken at 40× magnification. The scale bar is 50 μm.
Figure 13:
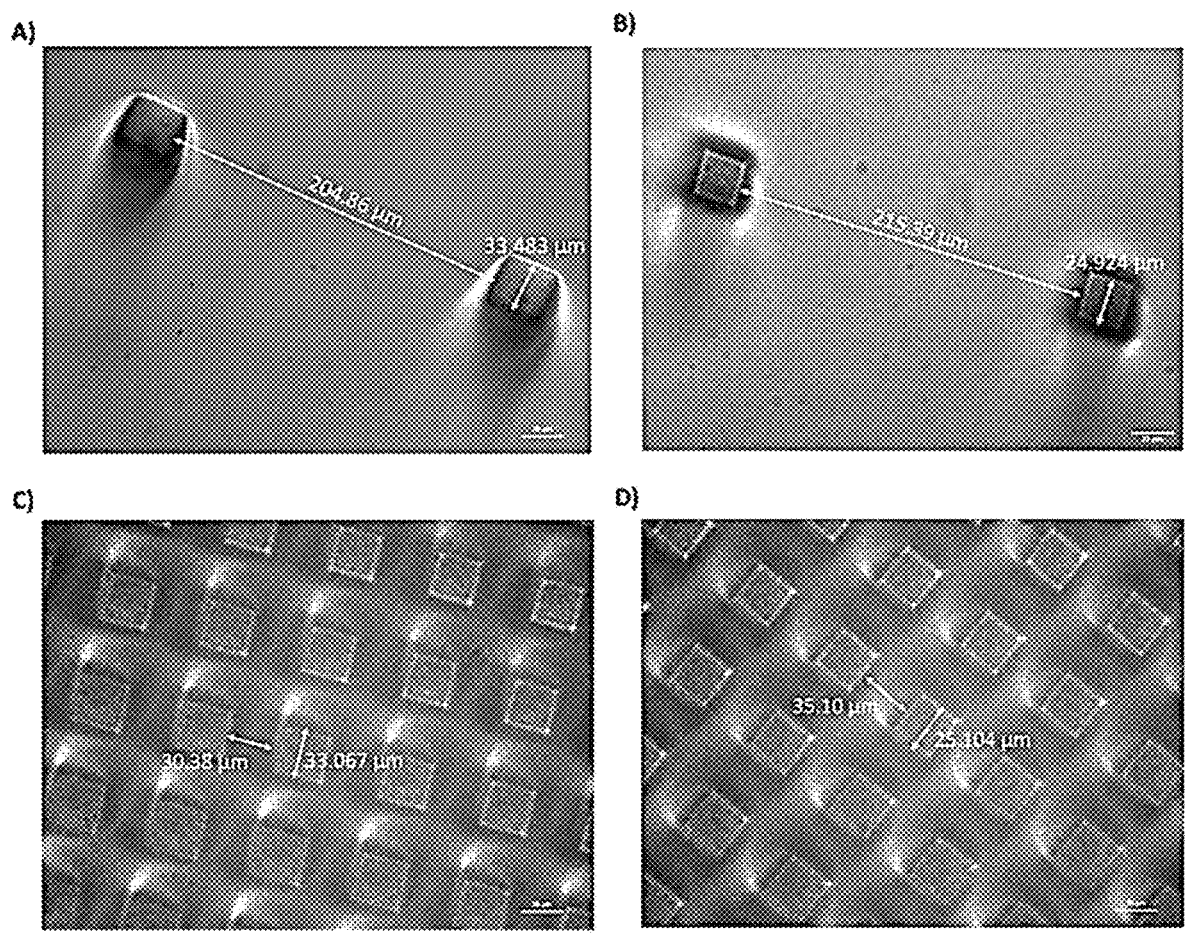
FIG. 13 illustrates microwells having a rectangular cross-section at different temperatures. The microwells are shown with measurements indicated at 37° C. (A, C) and at 25° C. (B, D). All images were taken at 40× magnification. The scale bar is 25 μm.

FIG. 12 and FIG. 13 illustrate, on a microscopic level, the temperature dependent swelling properties of typical temperature responsive cell culture microwells having circular cross-sections (FIG. 12) and square cross-sections (FIG. 13).

To assess cellular interaction with the platforms, MDA-MB-231 cells were manipulated and maintained in a humidified incubator at 37° C. with a 5% $CO_2$ atmosphere. Media components were filtered through 0.22 μm pore-sized filter units. Culture media consisted of RPMI-1640 medium supplemented with 10% (v/v) fetal bovine serum (FBS) and 1% penicillin/streptomycin.

When 80% confluency had been reached, the MDA-MB-231 cells were rinsed 3 times with 10 mL of phosphate-buffered saline (PBS) and trypsinized. The cells were pelleted by centrifuging the trypsin-media-cell solution at 2500 rpm for 5 minutes. The trypsin-media solution was aspirated, and the cells were fixed by incubating in 400 μL of 10% formalin at 37° C. for 10 minutes. The cells were again centrifuged at 2500 rpm for 5 minutes, and the formalin solution was aspirated. The cells were resuspended in 8 mL of a 300 nM DAPI stain and incubated for 15 minutes at room temperature. The cells were washed two times with PBS by pelleting via centrifuging and removing the solution.

The DAPI-stained cells were resuspended in enough PBS to yield a cell density of $1 \times 10^6$ cells/m L. 10 μL of the cell solution was pipetted on the microwell surface of the hydrogel along one edge of the microwell array. A 25×25 mL glass coverslip was placed on the edge of the pipetted cell solution at an obtuse angle. The angle of the coverslip was changed to an acute angle so that it contacted the cell solution. The coverslip was slowly wiped across the hydrogel microwells making sure the edge of the coverslip maintained full contact with the hydrogel surface. Excess cell solution was wiped off the edge of the hydrogel. Brightfield and fluorescence microscopies were used to verify the degree of microwell cell isolation. To increase the degree of microwell cell isolation, another 10 μL of the cell solution was pipetted and the wiping process was repeated.

Figure 14:
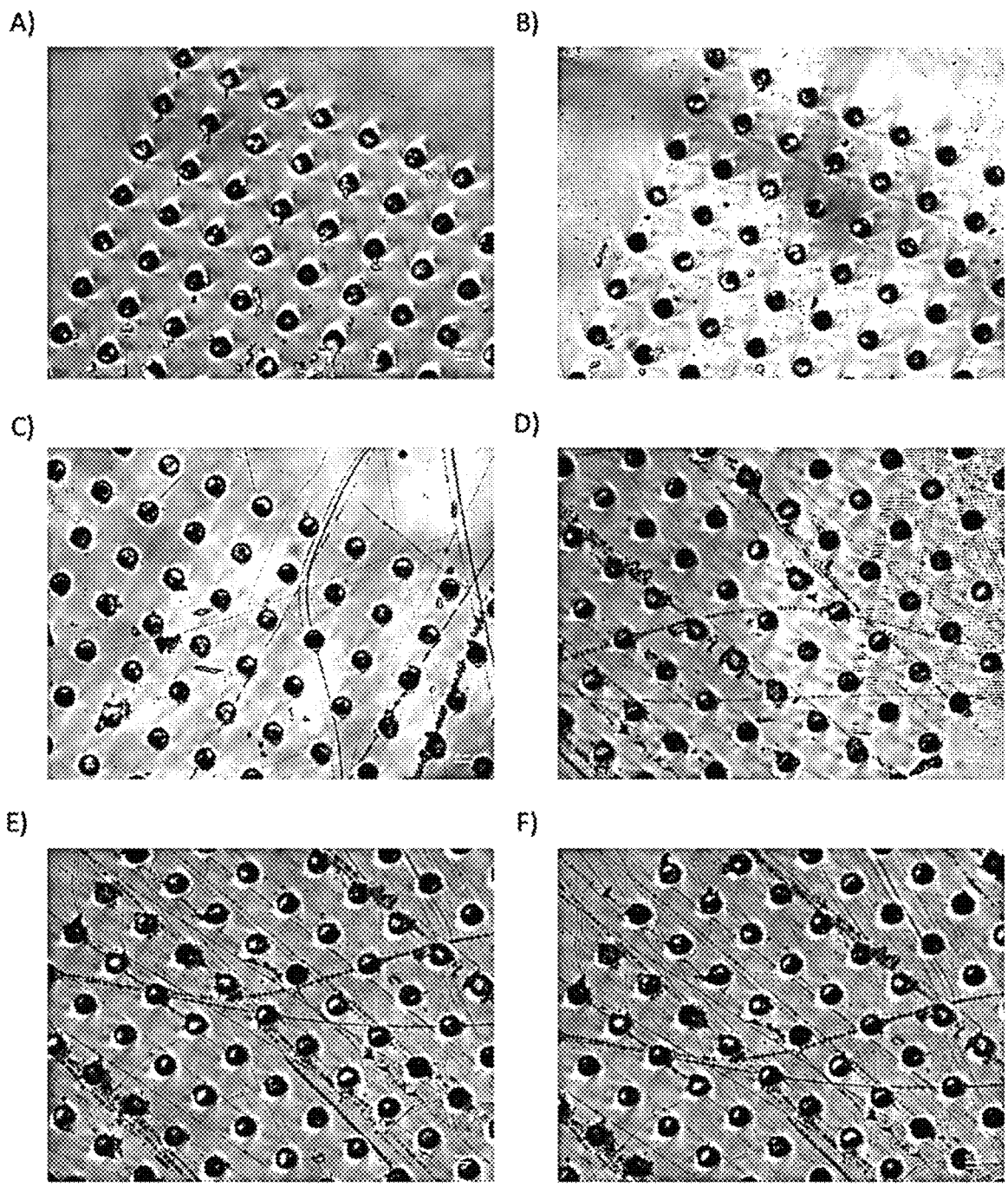
FIG. 14 presents overlay fluorescence and brightfield microscopy images of microwells encapsulating DAPI-stained MDA-MB-231 cells. The pipetting and wiping processes were performed at (A, B) 2×, (C, D) 3×, and (E, F) 4× repetition in an attempt to increase cell isolation throughput.

Through the simple pipet-wipe process, MDA-MB-231 cells were successfully encapsulated in circular microwells. Increasing repetitions of the pipet-wipe process roughly correlate to increased cell-microwell isolation efficacy. FIG. 14 demonstrates the efficiency in cell cluster isolation via the wiping process. Beneficially, due to the semi-translucent properties of the hydrogel, cell isolation was able to be visualized with brightfield microscopy and confirmed with cell nuclei staining.

Figure 15:
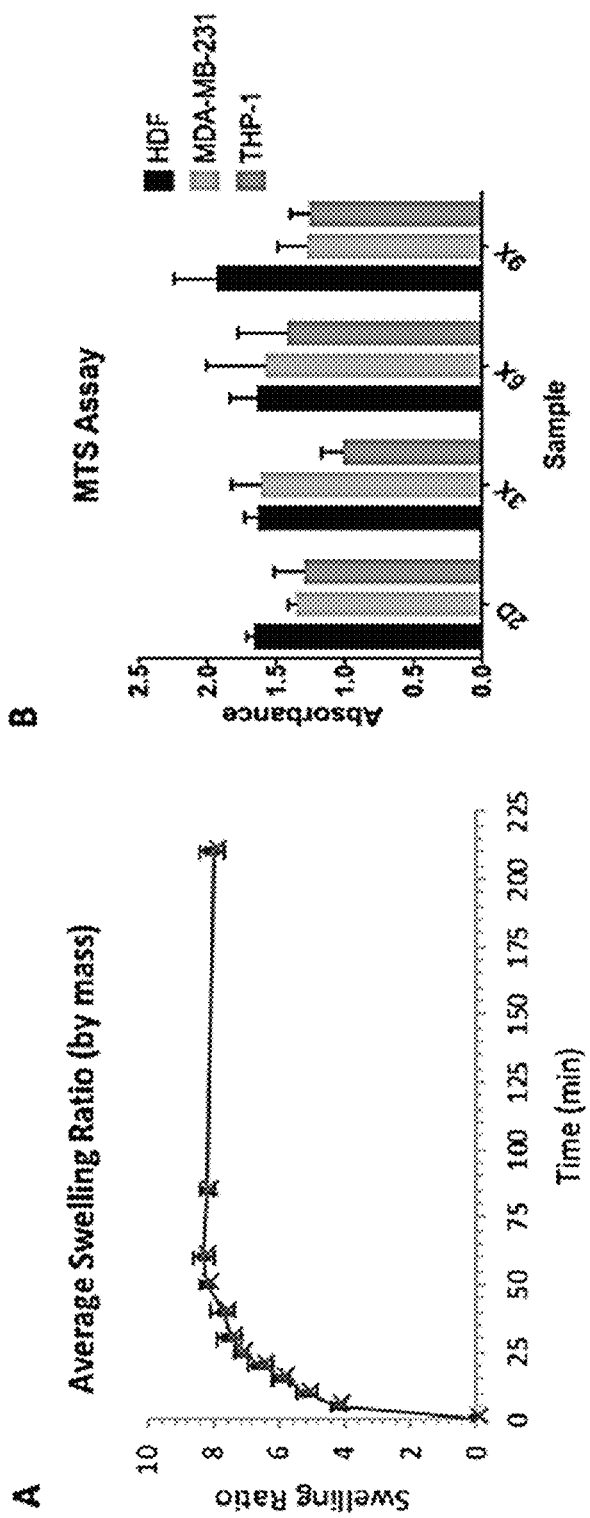
FIG. 15 graphically presents the swelling properties and cell biocompatibility of a cell culture platform assessed by A) periodic mass ratio measurements and B) MTS assay.

FIG. 15 presents results of the assessment of the swelling and cytotoxic effects of the thermoresponsive hydrogels. Results indicate that the hydrogel swells drastically within a few seconds and reaches near steady-state at approximately 30 minutes after transporting from 37° C. to 25° C. Furthermore, the hydrogel did not show any statistically-significant cytotoxicity towards three vastly different cell types, when compared to a 2D culture (control). MTS Assay was performed on three hydrogel samples of varying thermocycle purification and three different cell lines: HDF, MDA-MB-231, and THP-1.

The thermoresponsive hydrogel microwell platform showed no cytotoxic effects across three different cell types: breast cancer, monocytic, and fibroblast; this indicated the ability of the platform to be used for a vast number of cell types. Furthermore, the PNIPAM exhibited significant swelling within a matter of minutes after movement from 37° C. to 25° C. environments, reaching approximately 75% of steady-state mass after 20 minutes. Cells undergoing treatment using the PNIPAM hydrogel platform would spend approximately the same duration in the unfavorable 25° C. environment as a routine cell-passaging process in order to experience significant cell deformation.

While certain embodiments of the disclosed subject matter have been described using specific terms, such description is for illustrative purposes only, and it is to be understood that changes and variations may be made without departing from the spirit or scope of the subject matter.

What is claimed is:

1. A thermoresponsive device comprising:
   a supporting base layer comprising a first hydrogel including a first polymer; and
   a well layer at a surface of the supporting base layer, the well layer defining a well therein, the well layer comprising an interpenetrating polymer network hydrogel that includes a thermoresponsive polymer and a second polymer; wherein one or more walls of the well are formed of the interpenetrating polymer network hydrogel.

2. The thermoresponsive device of claim 1, wherein the first polymer and the second polymer are the same type of polymer.

3. The thermoresponsive device of claim 1, the well having a circular cross-section.

4. The thermoresponsive device of claim 1, the well having a non-circular cross-section.

5. The thermoresponsive device of claim 1, the well comprising a cross-sectional shape selected from a circle, a square, a rectangle, a triangle, a regular or irregular polygon, a star, or a letter.

6. The thermoresponsive device of claim 1, the thermoresponsive polymer comprising poly(N-isopropylacrylamide), poly(N,N-diethylacrylamide), poly(N-vinlycaprolactam), poly[2-(dimethylamino)ethyl methacrylate], or a combination thereof.

7. The thermoresponsive device of claim 1, the well layer further comprising a biologically active agent.

8. The thermoresponsive device of claim 1, wherein the well layer defines a plurality of wells therein, each of the plurality of wells including the interpenetrating polymer network hydrogel at one or more walls.

9. The thermoresponsive device of claim 1, wherein the well defines a microfluidic pattern in the well layer.

10. The thermoresponsive device of claim 1, wherein the first polymer and the second polymer are independently selected from a a polyacrylamide, poly(ethylene glycol) diacrylate (PEGDA), polyacrylic acid, poly(hydroxyethyl methacrylate) (PHEMA), poly(ethylene glycol) (PEG), poly (vinyl alcohol) (PVA), poly(acrylic acid) (PAA), poly(methacrylic acid) (PMAA), or combinations thereof.

11. The thermoresponsive device of claim 1, wherein the first polymer is a polymer that is not thermoresponsive at a temperature of from about 20° C. to about 50° C.

12. A method for forming the thermoresponsive device of claim 1 comprising:
   applying a precursor solution to the surface of the supporting base layer to form the well layer;
   polymerizing one or more components of at least a portion of the precursor solution to form the thermoresponsive polymer network hydrogel;
   following the polymerizing, removing a portion of the well layer to form the well in the well layer.

13. The method according to claim 12, further comprising forming the supporting base layer.

14. The method according to claim 12, wherein the step of polymerizing one or more components of at least a portion of the precursor solution comprises directing radiation at the precursor solution.

15. The method according to claim 14, further comprising masking a portion of the precursor solution from the radiation.

16. The method according to claim 15, the radiation comprising ultraviolet radiation.

17. The method according to claim 12, the precursor solution comprising a photoinitiator, a crosslinking agent, a polymerization inhibitor, a chain transfer agent, a salt, a surfactant, a buffer, a preservative, an antioxidant, a pigment, a humectant, or a biologically active agent, or any combination thereof.

18. A method for examining a cell, comprising:
   locating a cell in a well of the thermoresponsive device of claim 1; and
   modifying a temperature of the thermoresponsive device, wherein upon the temperature modification, a volume of the well is modified, the volume modification causing a mechanostimulation of the cell.

19. The method according to claim 18, wherein the cell is located in the well as a single cell or as a component of a cell cluster, a cell spheroid, or a cell organoid.

20. The method according to claim 18, wherein the temperature is modified cyclically.

21. The method according to claim 18, wherein the temperature modification begins or ends at a temperature of about 37° C.

22. The method according to claim 18, wherein the cell is encapsulated within the well in conjunction with an agent, the method further comprising delivery of the agent to the cell interior during or following the temperature modification.

23. The method according to claim 18, the method further comprising following the temperature modification, collecting a cell secretion from the well.

24. The method according to claim 18, the cell comprising a T cell, a dendritic cell, a cancer cell, a cardiac cell, a muscle cell, a stem cell, an adherent cell, or a non-adherent cell.

\* \* \* \* \*